United States Patent [19]

Smith, III et al.

[11] Patent Number: 5,639,810
[45] Date of Patent: Jun. 17, 1997

[54] INTERNALLY LUBRICATED ELASTOMERS FOR USE IN BIOMEDICAL APPLICATIONS

[75] Inventors: Hubert S. Smith, III, Denver; James M. Brugger, Boulder, both of Colo.; Helmut W. Frey, Williamsburg, Va.

[73] Assignee: COBE Laboratories, Inc., Lakewood, Colo.

[21] Appl. No.: 483,740

[22] Filed: Jun. 7, 1995

Related U.S. Application Data

[63] Continuation-in-part of Ser. No. 47,856, Apr. 15, 1993, abandoned.

[51] Int. Cl.$^6$ ............................................. C08K 5/24
[52] U.S. Cl. .................... 524/269; 524/297; 524/482; 524/463; 524/483; 524/484; 604/86; 604/88
[58] Field of Search ............................ 523/105, 210, 523/269, 297, 462, 463, 483, 484; 604/86, 88, 905, 167, 272, 274, 415

[56] References Cited

U.S. PATENT DOCUMENTS

| | | | |
|---|---|---|---|
| 2,992,940 | 7/1961 | Pace | 117/98 |
| 3,034,509 | 5/1962 | Bernstein et al. | 128/348 |
| 3,853,127 | 12/1974 | Spademan | 604/167 |
| 3,881,536 | 5/1975 | Doran et al. | 152/330 |
| 4,123,409 | 10/1978 | Kaelble | 523/118 |
| 4,177,182 | 12/1979 | Ichikawa et al. | 523/112 |
| 4,386,179 | 5/1983 | Sterling | 524/269 |
| 4,419,480 | 12/1983 | Tabor et al. | 524/525 |
| 4,481,323 | 11/1984 | Sterling | 524/269 |
| 4,496,348 | 1/1985 | Genese et al. | 604/167 |
| 4,511,354 | 4/1985 | Sterling | 604/98 |
| 4,552,914 | 11/1985 | Sterling | 524/269 |
| 4,578,413 | 3/1986 | Sterling | 524/269 |
| 4,613,640 | 9/1986 | Diesler | 524/264 |
| 4,684,672 | 8/1987 | Buchanan et al. | 523/100 |
| 4,781,680 | 11/1988 | Redmond et al. | 104/93 |
| 4,810,752 | 3/1989 | Bayan | 525/98 |
| 4,826,485 | 5/1989 | Johnson | 524/269 |
| 4,880,318 | 11/1989 | Shibahara et al. | 384/125 |
| 4,935,010 | 6/1990 | Cox et al. | 604/122 |
| 4,954,149 | 9/1990 | Fullermann | 46/105 |
| 4,978,714 | 12/1990 | Bayan et al. | 525/69 |
| 5,013,298 | 5/1991 | Moden et al. | 604/93 |
| 5,071,413 | 12/1991 | Utterberg | 604/283 |
| 5,080,654 | 1/1992 | Picha et al. | 604/167 |
| 5,082,875 | 1/1992 | Tajima | 523/103 |
| 5,127,626 | 7/1992 | Hilal et al. | 604/167 |
| 5,135,489 | 8/1992 | Jepson et al. | 604/48 |
| 5,143,963 | 9/1992 | Sterling et al. | 524/366 |
| 5,177,139 | 1/1993 | Klaar et al. | 524/484 |
| 5,207,656 | 5/1993 | Kranys | 604/256 |
| 5,209,737 | 5/1993 | Ritchart et al. | 604/167 |
| 5,211,634 | 5/1993 | Vaillancourt | 604/167 |
| 5,215,537 | 6/1993 | Lynn et al. | 604/244 |
| 5,254,097 | 10/1993 | Schock et al. | 604/167 |
| 5,279,571 | 1/1994 | Larkin | 604/167 |
| 5,324,256 | 6/1994 | Lynn et al. | 604/49 |
| 5,354,275 | 10/1994 | Behnke et al. | 604/86 |
| 5,385,553 | 1/1995 | Hart et al. | 604/167 |

FOREIGN PATENT DOCUMENTS

| | | |
|---|---|---|
| 2325672 | of 0000 | France . |
| 3518841A1 | 11/1986 | Germany . |
| WO93/01847 | 2/1993 | WIPO . |

OTHER PUBLICATIONS

C–Flex Product Information Sheet and Jun. 5, 1995 Information Disclosure Statement for USSN 08/047,856.

*Primary Examiner*—Edward J. Cain
*Attorney, Agent, or Firm*—Bruce R. Winsor; Edna M. O'Connor

[57] ABSTRACT

Improved elastomeric materials useful for medical and therapeutic device applications, such as penetrable septa, are described. In one aspect, the materials are deeply cleaned with solvent to significantly lower levels of undesirable organics. In another aspect, internally lubricated elastomer compositions compatible for use in medical and therapeutic device applications are provided. The lubricating fluid is present in the composition from about 0.5% to 50% by weight, and is initially substantially homogeneously dispersed in the elastomer. The fluid can be integrated into the elastomer by a solvent infusion method. In another aspect an internally lubricated thermoplastic septum, having an appropriate hardness for resealability with multiple penetrations, is provided.

70 Claims, 6 Drawing Sheets

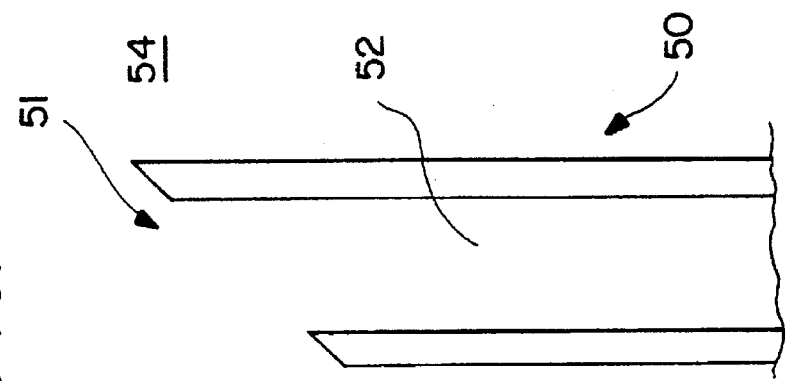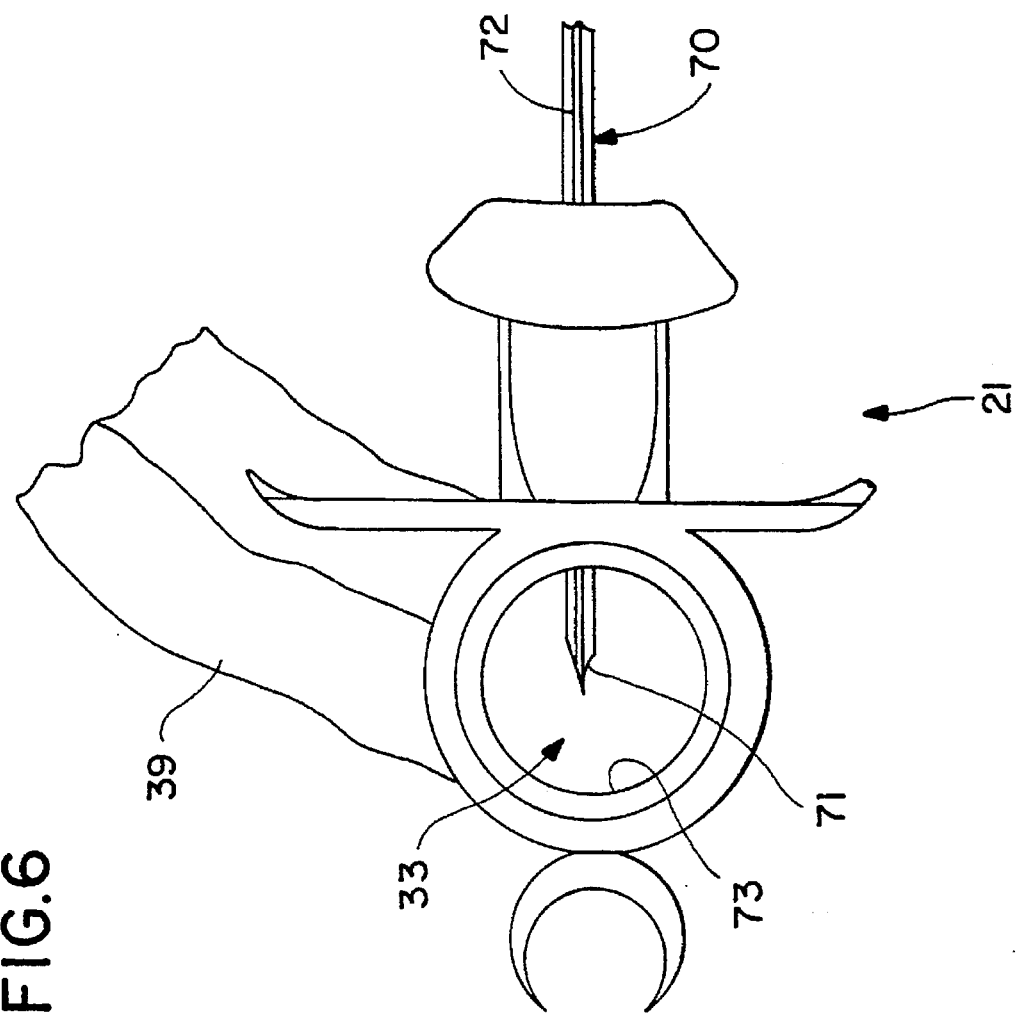

INTERNALLY LUBRICATED ELASTOMERS FOR USE IN BIOMEDICAL APPLICATIONS

CROSS REFERENCE PATENTS

This application is a continuation-in-part of application Ser. No. 08/047,856, filed Apr. 15, 1993 now abandoned, incorporated herein in its entirety.

FIELD OF THE INVENTION

The present invention relates to internally lubricated elastomeric materials suitable for use in biomedical applications. More particularly, the present invention relates to penetrable elastomeric materials used to construct septa for injection, withdrawal or monitoring of fluids employing needle syringes or related fluid withdrawal/injection devices.

BACKGROUND OF THE INVENTION

The medical device field is in constant need of improved, inexpensive, elastomeric material that combine biocompatibility with such elastomeric properties as flexibility, durability, and tear strength. In particular, with the risk of blood-borne infection to health care workers, such as AIDS and hepatitis, being such a serious concern today, there is a critical demand for improved, inexpensive, biocompatible elastomers for sealing and access applications for human systems. There is a particular demand for such elastomers in extracorporeal tubing systems, such as human infusion and dialysis systems.

The present invention provides means for improving elastomeric materials while maintaining biocompatibility. The present invention provides methods for treating elastomeric material, particularly inexpensive natural and synthetic rubbers, which significantly improves ease of use while decreasing the amount of undesirable organics that are extractable from the elastomer into physiological fluids. The methods provided minimize deterioration of desirable elastomeric properties of the material and instead result in improvement of certain properties. The methods provided are particularly useful for applications to penetrable elastomeric materials including applications of such materials in extracorporeal tubing systems.

One method involves deep cleaning of elastomers employing organic solvents. A second method involves introduction of lubricating fluids into elastomers to give more easily penetrable materials. A third method involves infusion of the elastomer with a solution of a lubricating fluid in an organic solvent to give internally-lubricated elastomeric materials having significantly lower levels of extractable organics.

The present invention also provides means for improving the integrity of apparatus used for the infusion, monitoring or withdrawal of fluid in extracorporeal tubing systems by using improved elastomers in the septa of such devices. Currently, such systems are single patient, single use disposable devices intended for relatively short-term use up to several days. A needle-penetrable barrier functions as the most convenient means for introducing or withdrawing fluids from a patient's extracorporeal tubing system. The penetrable barrier, or septum, allows access to the system while protecting the patient from external contamination and protecting others from contact with potentially dangerous patient body fluids.

The useful lifetime of any septum in the apparatus is decreased by repeated piercing which results in coring, tearing and abrasion of the septum. After repeated use, the septum can also leak, compromising the integrity of the system, and may release debris into the system. The useful lifetime of extracorporeal tubing apparatus can be increased by employing a septum material that has improved resistance to coring, tearing and abrasion.

Septa currently employed in biomedical applications are typically natural rubber, synthetic polyisoprene rubber or silicone rubber. These materials are typically difficult to penetrate and display rapid deterioration on repeated piercing with the large gauge needles (18 and 20 gauge) that are often used for blood sampling and fluid infusion.

It is desirable that septa allow penetration for fluid access with minimum force of insertion to lessen the danger of either damage to the apparatus or injury to the patient or health care worker while maintaining a sealed system. One well known prior art solution for reducing the risk to patients and health care workers is to blunt the needle that penetrates the septum such that it is not sharp enough to penetrate skin unless an undue force is exerted on it. This has required that the septum be pre-slit or lanced, and provisions made for guiding the blunt needle into the correct orientation on the septum. This solution has failed, at least in part, because the blunt needle tends to gall or core the septum material. As a result, small pieces of septum material are potentially released into the patient's blood stream. This is particularly worrisome where septum material is released into a patient's venous blood stream because the contaminating material may potentially enter a patient's brain via the venous pathway.

The inventors have found that significantly improved elastomeric septa for biomedical applications can be produced by dispersing a lubricating oil, such as a silicone oil or a mineral oil, throughout an elastomeric material, such as a natural or synthetic rubber. It is desirable for the resulting composition to have a Shore A durometer hardness in the range of 15 to 40. The resulting internally lubricated septa display dramatically lowered resistance to penetration with surprisingly improved resistance to deterioration on piercing, improved resealing properties, and improved tearing and coring resistance. In addition, these internally lubricated septa display surprisingly lowered levels of undesirable organic extractables, making them even more attractive for medical device applications.

In one embodiment, the inventors have found that using a thermoplastic elastomer, a styrene-ethylene/butylene-styrene block copolymer internally lubricated with a silicone oil having a Shore A durometer hardness in the range of 15 to 40, and sold under the name C-FLEX® by Consolidated Polymer Technologies, Inc., to construct septa offers significant advantages over the prior art. Using this thermoplastic elastomer allows the septum to form an un-pierced, continuous seal through which a blunt or sharp needle can be penetrated. Un-pierced is herein defined as not having a preformed opening prior to the first needle penetration. The septum will then form a transient opening around the needle allowing fluid to be removed from, added to and/or monitored in the extracorporeal tubing system. After the needle is removed from the septum, the transient opening reseals automatically once again forming a continuous seal with satisfactory leak resistance for the useful life of the septum. The useful life of the septum is defined as at least six penetrations. Due to this automatic resealing characteristic, the septum of the thermoplastic elastomeric embodiment of the present invention is defined as self-sealing.

The thermoplastic elastomeric embodiment or second preferred embodiment of the present invention, therefore, does not require pre-slitting or lancing during manufacture. Furthermore, the thermoplastic seal may be manufactured using plastic injection molding, significantly reducing the cost and increasing the ease of manufacture. The invention's configuration also renders the septum/needle alignment notably less critical than for the prior art. The invention is therefore safer and easier to use.

Attempts to improve the design of septa for extracorporeal tubing systems have included:

U.S. Pat. No. 5,324,256 (1994) and U.S. Pat. No. 5,215,537 (1993) to Lynn et al. disclose elastomeric septa for coupling intravenous conduits. Lynn ('256) discloses a blunt cannula surrounded by a shroud that is sharp enough to penetrate an unperforated rubber septa but not sharp enough to penetrate human skin when a casual force is exerted on it. Lynn ('537) discloses an embodiment that provides a septum having a continuous un-pierced surface with a weakened core. A blunt cannula can then be forced through the septum at the weakened core. The thermoplastic elastomeric embodiment of the present invention, on the other hand, is composed of a uniformly strong internally lubricated thermoplastic elastomer that does not require a weakened core or sharpened cannula for penetration.

U.S. Pat. No. 5,209,737 (1993) to Ritchart et al. discloses a septum for surgical trocars. The disclosed septum is composed of C-FLEX®, the same thermoplastic elastomer used in the second preferred embodiment of the present invention. The disclosed '737 invention, however, does not disclose an unpierced septum, but rather provides the C-FLEX® septum with an adjustable orifice for receiving and sealing around a surgical instrument. The orifice is adjusted via a lever system. The preferred embodiment of the present invention, employing C-FLEX®, does not require an orifice and resealing means. The C-FLEX® preferred embodiment of the present invention is initially manufactured as a continuous unpierced seal and automatically reseals once the probe or cannula is removed.

U.S. Pat. No. 5,207,656 (1993) to Kranys discloses a medical instrument valve, such as a hemostasis valve in a catheter introducer, having an un-pierced, foamed, elastomeric septum for receiving a solid elongated member, such as a guide wire. Kranys ('656) does not disclose lubricating the elastomeric material of the septum itself. Rather, fluid, including lubricating fluid, may be contained in the cells of the foam. Furthermore, the Kranys ('656) invention is designed to receive solid elongated members for a limited number of penetrations.

The present invention comprises an internally lubricated elastomeric septum for use with cannulas that is not foamed and, therefore, does not contain internal cells. Using a foam with a hollow member, such as a cannula or conventional needle, could result in serious coring problems, particularly with large gauge needles. Foamed elastomers also have a lower tensile strengths than internally lubricated elastomers. The lower tensile strength of foam renders it less durable and resealable than an internally lubricated solid, as well as increasing the risk of galling and coring. Furthermore, it is very possible that blood could enter the cells of a foam septum, coagulate and be released back into the blood stream when the foam septum is penetrated again, resulting in thrombosis problems if repeatedly penetrated.

U.S. Pat. No. 5,080,654 (1992) to Picha et al. discloses a fluid injection device for an intravenous delivery system having an access port with a closure element, where the closure element has a preformed central passage for receiving a blunt injection probe. The elastomeric septa of the present invention are un-pierced and do not require a preformed passage for receiving a blunt probe.

U.S. Pat. No. 4,496,348 (1985) to Genese et al. discloses a venipuncture device having a solid, elastic septum which is penetrable by a sharpened tip. Upon removal of the sharpened tip, a spring-loaded compression mechanism applies a compressive force against the elastic septum, thereby resealing the opening. The septa of the present invention may be used with a blunt cannula and do not require a spring-loaded compression device for resealing. The septa of the present invention are self-sealing.

U.S. Pat. No. 4,935,010 (1990) to Cox et al. discloses a valve having an elastomeric septa having a preformed zone of weakness for receiving a blunt cannula. The disclosed zone of weakness is a cruciform cut that extends completely or partially through the length of the septa. In contrast, the present invention provides an un-pierced, uniformly strong, continuous septum that is penetrable by a blunt or sharp needle.

Attempts to improve the resealability of elastomeric sealing members, such as septa, have included:

U.S. Pat. No. 3,853,129 of Spademan in which non-uniform stress is induced normal to the longitudinal axis of the septum to facilitate resealing; U.S. Pat. No. 5,135,489 of Jepson et al. in which axially directed force is applied to reseal a pre-split septum; and U.S. Pat. No. 4,954,149 of Fullerman in which a septum having a pre-cut annular injection passage is sealed by a duckbill seal.

Attempts to provide improved materials for penetrable rubber closures have included:

U.S. Pat. No. 5,082,875 of Tajima et al. which describes synthetic rubber compositions containing high molecular weight polyethylene (HMPE, MW $10^6$ to $10^9$) which are said to have good tensile strength and elongation properties;

U.S. Pat. No. 4,684,672 of Buchanan et al. which relates to high tear-strength natural or synthetic rubber compositions comprising high density polyolefin, a filler and a multi-functional activator to cross-link the rubber and polyolefin; and U.S. Pat. Nos. 4,810,752 and 4,978,714 of Bayan et al. which describe elastomeric compositions with low hardness, low coefficients of friction, and reduced stickiness which provide good barriers to moisture and oxygen. The composition combines a dynamically vulcanized butyl rubber with uncured organopolysiloxane grafted EPDM polymers.

The following references may also be considered relevant to the present invention:

U.S. Pat. No. 5,177,139 to Klaar discloses a composition useful as a sealing strip or molding in the construction industry. The composition is composed of polyolefin rubber and polyethylene having a critical melt flow index value and a mineral oil. The composition is said to have improved elongation and tensile strength with respect to application as a roof sealing strip.

U.S. Pat. No. 4,123,409 of Kaeble describes a thermoplastic sealing material for contact with animal tissue. An elastomeric material with thixotropic properties combining a high molecular weight non-volatile oil in at least a ratio of 1 to 1 with a block copolymer is described. The material is said to be flexible and conformable to the skin and to provide a wetting-type property. Thermoplastic block copolymers having polystyrene end blocks and butadiene or isoprene intermediate blocks are combined with a hydrocarbon oil, e.g., mineral oil, compatible with the intermediate block. Thermoplastic block copolymers having polyalphamethylstyrene end blocks and polydimethylsiloxane intermediate blocks are combined with silicone oil. Molded articles made with these materials are said to combine conformability and flexibility with adherence strength and resistance to tearing.

U.S. Pat. No. 5,143,963 of Sterling et al. describes elastomeric compositions having fluorocarbon oils, gums or greases dispersed there through. The compositions have fluorocarbon-like surface properties which are said to be advantageous for medical applications, having superior biocompatibility for medical tubing, implants, etc.

U.S. Pat. No. 4,386,179 (1983) to Sterling, and 4,481,323 to Sterling relate to thermoplastic elastomer compositions having a uniformly dispersed (0.1 to 8%, or 0.1 to 12%) polysiloxane or silicone oil throughout the composition. These compositions are said to be useful in medical applications, for example, as inflatable cuffs or balloons in endotracheal devices. Articles made from these materials are said to have a smooth surface, like a silicone polymer, which is less irritating for skin contact. Compositions include hydrocarbon block copolymers, such as styrene-ethylene-butylene-styrene copolymers, to which silicone oil and optionally mineral oil are added. The disclosures discuss the partial migration of the silicone to the surface of the material. Related U.S. Pat. No. 5,511,354 (1985) to Sterling, derived from a divisional application of '179 and claims the use of the material disclosed in '179 for use as an inflatable cuff, particularly an inflatable cuff surrounding the shaft of an endotracheal tube. Related U.S. Pat. No. 4,578,413 also to Sterling, describes polymeric tubing composed of the same thermoplastic elastomer compositions useful for medical applications, particularly for tubing with improved flex-life, low spallation in roller-type applications, and decreased debris production. The disclosures of U.S. Pat. Nos. 4,386,179 (1983), 4,481,323 (1984), 4,511,354 (1985) and 4,578,413 (1986) to Sterling and U.S. Pat. No. 4,613,640 (1986) to Deisler are herein incorporated by reference in their entirety.

In particular, Sterling ('179) describes a composition including an elastomeric thermoplastic block copolymer having polysiloxane (0.1–8%) dispersed throughout. The composition is formed by melting elastomeric crumbs mixed with polysiloxane and subjecting the melted mixture to a shearing pressure, for example by extruding under pressure of 2500 p.s.i. or greater. The pressurized extruding process appears necessary to achieve the disclosed properties. Those disclosed properties include the ability to be extruded into extremely thins sheets (0.005 inch or less), a high degree of elasticity, and a greater concentration of polysiloxane at the immediate surface of the material than internally. The disclosed medical uses include a balloon cuff for an endotracheal tube and a cellular sponge like material for padding wounds. Flexibility and capacity to be extruded into thin sheets appear to be the most important characteristics of the composition.

Surprisingly, we have found that certain variations on compositions of the internally lubricated thermoplastic elastomer generally disclosed in '179, '323, '354 and '413 to Sterling and in '640 to Diesler, are useful as penetrable septa in applications that require multiple penetrations. To be useful for penetrable septa that will be penetrated multiple times, a chosen material should possess an appropriate amount of hardness for resealability to needle puncture, ease of penetration, flexibility, resistance to coring and galling, and tear strength. An appropriate hardness for resealability to needle puncture falls in the range of about 15 to about 40 on the Shore A durometer hardness scale. A material having a hardness in this range will not leak when penetrated at least six times at the same insertion site. Materials having a Shore A durometer hardness greater than about 40 are not likely to reseal adequately after puncture and, therefore, are likely to leak.

The disclosures of '179 and '354 do not disclose the Shore A durometer hardness of the claimed compositions, nor suggest that the claimed compositions would reseal after multiple punctures. The disclosure of '323 describes compositions having Shore A durometer hardnesses of at least 44 or greater. The disclosure of '413 describes compositions having Shore A durometer hardnesses of at least 50. Surprisingly, we have found that if certain compositions of the internally lubricated thermoplastic elastomer generally disclosed in '179, '323, '354 and '413 are modified to bring their Shore A hardness within the range of 15 to 40, they are easily penetrable, resistant to coring and galling and capable of withstanding repeated punctures without leakage.

It is also surprising that compositions generally disclosed in '179, '323, '354 and 413 are easily penetrable because the disclosures of these patents teach that the internal lubricant, polysiloxane, tends to concentrate at the immediate surface of the material rather than uniformly dispersing throughout the material. Furthermore, the disclosures of the Sterling patents do not suggest that the disclosed compositions or modifications thereof possess the combination of characteristics necessary for a penetrable septa that will be used in applications requiring multiple penetrations.

U.S. Pat. No. 4,613,640 (1986) to Deisler et al. discloses a composition comprising an elastomeric thermoplastic block copolymer, mineral oil and polysiloxane which is miscible in mineral oil. The composition is said to be an improvement compositions previously disclosed by Sterling in U.S. Pat. No. 4,386,179 (cited herein) and U.S. Pat. No. 4,481,323 (cited herein). The improvement is to increase the transparency of the material for use as container or tubing. Corresponding with these uses, the Deisler ('640) reports Shore A durometer hardnesses ranging from 49 to 70.

U.S. Pat. No. 4,177,182 of Ichikawa et al. relates to polyvinyl chloride resin compositions comprising 100 parts by weight of polyvinyl chloride series resin, 20–80 parts by weight of a plasticizer, and 0.2 to 7 parts by weight of silicone oil. The silicone oil is said to minimize the elution of the plasticizer from the resin. These resins are said to be well adapted for uses in food containers and medical products, particularly for the collection, preservation and administration of physiological solutions.

U.S. Pat. No. 3,034,509 of Bernstein et al. describes surgical tubing made with a polyethylene to which 0.5 to 1% by weight silicone oil has been added. The silicone oil is said to reduce toxic reaction to the tubing and to inhibit blood coagulation upon contact with the tubing.

U.S. Pat. No. 2,992,940 of Pace relates to elastomeric flexible cellular materials from polyisocyanates which are treated by external application of silicone oil or by injection of silicone oil into the cellular structure to eliminate internal tack.

SUMMARY OF THE INVENTION

A significant object of the present invention is to provide improved medical and therapeutic devices, particularly penetrable sealing elements, septa and membranes, using improved elastomeric materials.

Another object of the present invention is to provide a biocompatible septum that will not contaminate a patient's blood stream with foreign septum material.

Another object of the present invention is to provide a septum that will not contaminate a patient's blood stream with septum material due to coring or galling.

Another object of the present invention is to provide a septum for an access portal with improved resealability with repeated puncture.

Another object of the present invention is to provide an access port for an extracorporeal tubing system in which the needle to septum alignment is not critical.

Another object of the present invention is to provide an unpierced, continuous septum for use with either a blunt or sharp needle or probe.

Another object of the present invention is to provide a septum that does not require the added manufacturing step of pre-slitting or lancing to form an aperture to receive a blunt probe.

Another object of the present invention is to provide a septum for an extracorporeal tubing system that may be formed by injection molding and is, therefore, inexpensive and easy to manufacture.

In accordance with these objectives, one aspect of the present invention provides solvent-washed, deep-cleaned elastomeric materials which have significantly lower levels of undesirable extractable organics than untreated elastomers. Solvent-washed elastomers are improved over analogous untreated elastomers for use as penetrable sealing elements in medical devices. Elastomeric materials are placed in an organic solvent for an extended period of time from 1 h to 24 h, but more typically 4 to 8 h, in order to remove residual undesirable organics. Elastomers are then removed from the solvent bath and dried. Solvents useful for elastomer cleaning include methylene chloride, perchlororthylene, and freons, among others. Natural and synthetic rubbers, particularly those that are peroxide-cured, display dramatically improved results in toxicology tests after washing with volatile organic solvents, e.g., methylene chloride.

In a second aspect, internally lubricated elastomer compositions compatible for use in medical and therapeutic device applications are provided. The elastomer compositions provided comprise from about 0.5% to 50% by weight of a lubricating fluid initially substantially homogeneously dispersed in the elastomer. The lubricating fluid functions to internally lubricate the elastomer decreasing the internal coefficient of friction and increasing the ease of needle penetration of the material and increasing the durability of the material to repeated penetration. The internally lubricated elastomers of this invention retain excellent elastomeric properties.

A preferred method for making internally lubricated elastomers of this invention is by solvent infusion. The levels of undesirable organics, made by the preferred method, that are extractable from the internally lubricated elastomer into physiological fluids are also decreased. The elastomer is contacted with a solution of a lubricating fluid, preferably about 0.5% to 20% by weight, in an organic solvent to allow the lubricating fluid to infuse into the elastomer such that the lubricating fluid becomes substantially homogeneously dispersed there through. After soaking the elastomer in the solution for an extended period of time, from 1 h to 24 h, but typically from about 4 h to 8 h, the elastomer is removed from the solution and the solvent is removed from the elastomer. A treated, infused elastomer contains individual concentrations from 0.5% to 50% of the lubricating oil depending on the type of oil and elastomer used. Solvents that can be used in the infusion method include methylene chloride, perchloroethylene, and freons, among others.

Elastomers of this invention include, but are not limited to, natural and synthetic rubbers, polyurethanes, polyolefins, thermoplastic elastomers, silicone rubbers, and fluorocarbon elastomers. Useful lubricating fluids include, but are not limited to, silicone oils, mineral oils, hydrocarbon oils, aromatic oils, vegetable oils and fluorocarbon oils.

A preferred thermoplastic elastomer of the present invention is a styrene-ethylene/butylene-styrene block copolymer internally lubricated with 0.5 to 50% w/w polysiloxane oil having a Shore A durometer hardness of 15 to 40. This thermoplastic elastomer is commercially available from Consolidated Polymer Technologies, Inc. under the name C-FLEX®. Particularly preferred are C-FLEX® R70-214 and R70-028. Preferred thermoset elastomer compositions are natural or synthetic rubbers having an initial concentration from about 0.5% to 50% silicone oil dispersed there through and a Shore A hardness of about 15 to 40.

Internally lubricated elastomers useful in therapeutic or medical device applications as penetrable septa, membranes or like barrier or sealing materials are provided. In particular, internally lubricated septa for use in fluid access sites for human infusion apparatus are provided. Natural and synthetic rubber elastomers, particularly synthetic polyisoprene, having silicone oil dispersed there through are provided for septa applications. Thermoplastic elastomers, having silicone oil dispersed there through, are also provided for septa applications. The septa of the present invention made of internally-lubricated elastomers are improved in ease of use, ease of needle penetration, durability to piercing, and have higher resistance to abrasion and coring than septa made of the analogous non-lubricated elastomers. The subject septa reseal adequately to prevent leaks for at least 6 penetrations with a sharp needle having a gauge smaller or equal to 18 and a blunt needle having a gauge smaller than or equal to 20, when the needle penetrations are made in substantially the same location of the septum with fluid at room temperature and under at least about 100 mmHg.

The present invention also provides an internally lubricated thermoplastic elastomeric access port for an extracorporeal tubing system through which fluid can be added to, removed from or monitored in the system. This embodiment consists of a rigid plastic housing that interfaces with the extracorporeal tubing system at the housing's first end and provides and access port at the housing's second end. A channel connects the interior of the extracorporeal tubing system with the access port.

The access port of this embodiment can be sealed against contaminants by a thermoplastic elastomeric plug that forms an un-pierced, resealable, continuous septum. The thermoplastic elastomer may be constructed of a styrene-ethylene/butylene-styrene block copolymer internally lubricated with polysiloxane oil having a Shore A durometer hardness of 15 to 40 commercially available from Consolidated Polymer Technologies, Inc. under the name C-FLEX®.

A blunt or sharp probe is forced through the thermoplastic septum, into the connecting channel and lastly into the tubing system interior. The blunt probe is insufficiently sharp to penetrate skin unless pressure greater than that required to penetrate a septa is exerted on the blunt probe. The septum forms a transient opening around the needle allowing fluid to be removed from, added to, or monitored in the system. Once the needle is removed from the septum, the transient opening reseals once again forming a continuous, fluid tight seal for at least six penetrations.

Other objects of this invention will appear from the following description and appended claims, reference being had to the accompanying drawings forming a part of this

BRIEF DESCRIPTION OF THE DRAWINGS

FIG. 6 is a side view of the FIG. 3 preferred embodiment of the present invention fully assembled and engaging a sharp needle.

FIG. 7 is a cross sectional view of the blunt probe shown in FIG. 4.

DETAILED DESCRIPTION OF THE INVENTION

Figure 1:
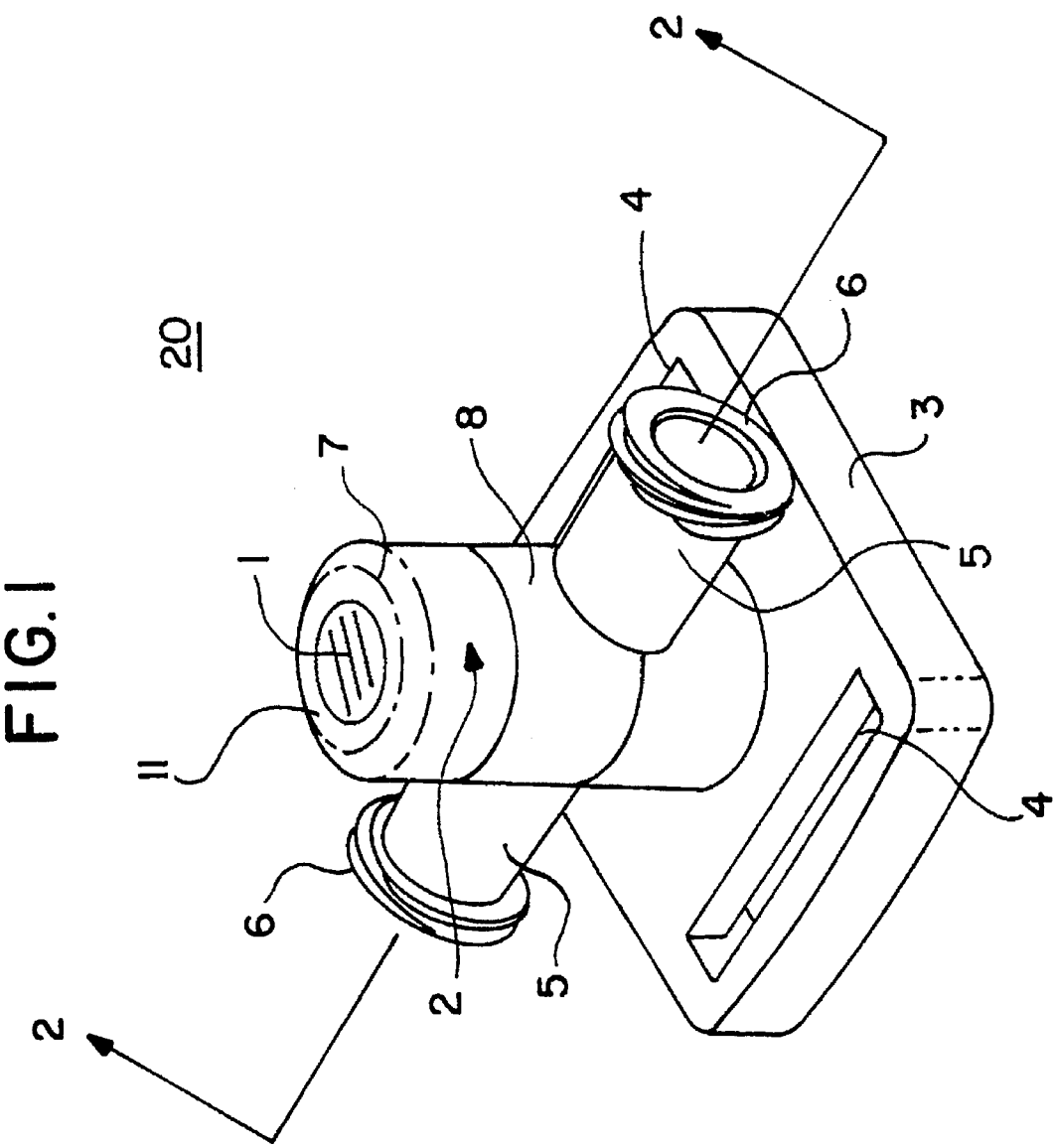
FIG. 1 is a schematic drawing of a fluid access site with a septum of a first preferred embodiment of the present invention.

Elastomers appropriate for use in this invention include natural or synthetic rubbers, polyurethanes, polyolefins, such as grafted EPDM polymers, thermoplastic elastomers such as styrene block copolymers, silicones, and fluorocarbon elastomers. In general, the methods of this invention can be employed with any elastomer that is compatible for use in medical or therapeutic applications. Elastomers, for example, must be capable of withstanding multiple sterilization cycles.

Preferable elastomers are those having the flexibility, tear strength and hardness for resealability to needle puncture necessary for use as penetrable seals, membranes or septa. It is important that a chosen elastomer is capable of resulting in a composition possessing a hardness commensurate with a compression set appropriate for use in penetrable seals, membranes or septa that will be penetrated multiple times. A compression set measures the tendency of a hole, created by a penetrating needle, to remain open and, thus, leak after the needle is withdrawn. Compositions comprising a Shore A durometer hardness in the range of 15 to 40 possess compression sets that indicate that they will reseal adequately after multiple punctures.

Elastomers appropriate for use as such seals must also be capable of forming a oxygen- and water-excluding barrier between an internal fluid environment, such as in an infusion apparatus, and the external environment. Elastomers can be thermoplastic or thermoset elastomers which can be cured or cross-linked by any method known in the art. Natural and synthetic rubbers can be cured by any known method.

Those elastomers to which lubricating fluid is added must be dense enough to hold and retain a lubricating fluid to the desired level between about 0.5% to 50% without excessive bleeding of oil which would detrimentally affect biocompatibility of the treated elastomer and result in loss of improved elastomer properties.

Organic solvents employed in the deep cleaning of elastomers are typically halogenated hydrocarbons. In general, preferred solvents are those that penetrate the elastomer to remove undesired impurities while causing no unacceptable level of detrimental effect to the properties of the elastomer. The solvent should be volatile, such that it can be readily removed from the elastomer after washing.

Lubricating fluids of this invention are liquid at room temperature have viscosities in the range of about 10 to 10,000 cs at room temperature (RT) and include among others silicone oils, mineral oils, hydrocarbon oils, aromatic oils, flurocarbon oils, vegetable oils, and fish oils. It is preferred that the oil itself be biocompatible causing no significant toxic or irritant reaction with human tissue and having no such effect when used in medical devices, particularly in human infusion devices. High purity, ultra-high purity or medical grade lubricating fluids are preferred.

The lubricating fluid is chosen to have a chemical composition and molecular weight such that the oil can be readily dispersed into a given elastomer to a desired initial concentration between about 0.5% and 50% by weight without extensive oil bleed thereafter during use in devices. Depending on the elastomer, lower molecular weight lubricating fluids generally infuse to a higher concentration into the elastomer than higher molecular weight fluids. The lubricating fluid may have a chemical composition that is compatible or incompatible with the major component in the elastomer. It is preferred to choose the lubricating fluid to minimize the bonding interactions between molecules of the lubricating fluid and the major elastomer component. It is believed that minimizing such interactions by choice of incompatible lubricating fluids improves the internal lubricating properties of the treated elastomer and improves the resealability and durability of the treated elastomers to repeated needle piercings. It may be desirable in some applications to devolatilize the lubricating fluid.

The inventors have found that silicone oil lubricated polyisoprene rubber septa prepared by treating polyisoprene No. 100-35, Gardena Rubber Co., Gardena, Calif., have substantially greater durability to penetration than lubricated septa prepared from other polyisoprenes tested to date. Thus, the polyisoprene embodiments of the internally lubricated septa of this invention are the Gardena 100-35 polyisoprene septa infused with silicone oil.

Silicone oils employed in the methods and products of this invention are those that are fluid at room temperature ("RT"). They include, but not limited to, those that have viscosity between about 10 to about 10,000 centistokes (cs) (RT) or that have molecular weights in the range from about 1200 to about 62,000. Silicone oils having viscosities in the range of about 20 to 100 cs (RT) are preferred for preparation of penetrable rubber septa. Silicone oil having viscosity of about 50 cs is more preferred for treatment of synthetic isoprene septa. Useful silicone oils include polysiloxanes having lower alkyl groups, aryl groups or both as substitutents. Aryl substitutents include phenyl groups. Lower alkyl substitutents include alkyl groups having from one to six carbon atoms, and preferred lower alkyl substitutents are methyl and ethyl groups. Silicone oils having terminal polar groups, such as hydroxy, or amino substitutents or those in which a low percentage, preferably lower than about 10%, of the substituents of the siloxane are such polar substitutents are useful, particularly in combination with natural or synthetic rubbers, so long as the oil retains an essentially non-polar character. Silicone oils having unsaturated substituents, such as vinyl groups, are useful in preparation of lubricated elastomers, as long as cross-linking of the oil with the elastomer is minimized.

Preferred silicone oils of this invention are polydimethylsiloxane, polydimethyldiphenylsiloxane and polydiphenylsiloxane. The choice of siloxane will depend on the application of the treated elastomer, the desired amount of oil infusion and the chemical composition of the elastomer. Different substituted polysiloxanes will be more or less suitable with different elastomers. For example, polydimethylsiloxane was found to be particularly suitable for the preparation of improved synthetic isoprene rubber septa.

Suitable mineral oils include those having viscosities in the range of about 10 to 10,000 cs (RT) obtained from petroleum by separation or refining and can include paraffinic hydrocarbons, olefinic hydrocarbons, aromatic hydrocarbons, and mixtures thereof. The choice of mineral oil for combination with a given elastomer will depend on the chemical composition of the elastomer, the molecular weight of the oil and the desired end product and use. Mineral oils may be combined with any elastomer compatible in biomedical applications but are preferably combined with silicone rubbers.

Fluorocarbon fluids having viscosities in the range of about 10 to 10,000 cs (RT) are suitable for use in this invention and include fluorinated hydrocarbon oils, fluorinated polyethers, and perfluorinated hydrocarbons and perfluorinated polyethers, among others. Fluorocarbon lubricating fluids may be combined with any elastomer compatible in biomedical applications but are preferably combined with fluorocarbon elastomers.

Natural oils, such as vegetable and fish oils, can also be used in this invention. Soybean oil, castor oil, corn oil, cotton seed oil, fish oils, deodorized fish oils, cod-liver oil, squalene and any other edible oil are useful as lubricating fluids for elastomers. Vegetable and other natural oils may be combined with any elastomer compatible in biomedical applications.

Other lubricating fluids that have been found to produce elastomers with improved ease of penetration and durability to penetration when infused or otherwise combined into elastomers include: glycerin, triglyceride oil and Benzoflex™. Introduction of glycerin, triglyceride oil or Benzoflex™ into natural or synthetic rubbers particularly polyisoprene rubbers, results in improved internally lubricated rubber materials.

Lubricated elastomers may optionally include minor amounts of accelerating agents, antioxidants, plasticizers, curing agents, cross-linking agents, and processing aids as well as fillers, binders, and pigments, alone or in combination, so long as biocompatibility of the lubricated elastomer is retained and the function of the elastomer is not adversely affected. To obtain the subject lubricated elastomers having a Shore A durometer hardness of about 15 to 40, the content of fillers, cross-linking agents, block compositions, and plasticizers can be adjusted. As is known by those skilled in the art, the hardness of thermoset elastomers can be increased by the addition of cross-linking reagents and the hardness of thermoplastics can be increased by the addition of rigid block compositions (e.g. polystyrene). For all elastomers, the addition of fillers increases hardness and addition of plasticizers decreases hardness. The desired hardness in a particular lubricated elastomer composition can be obtained by employing methods known to those of skill in the art.

Internally lubricated elastomers can be prepared by any method which results in a substantially uniform distribution of the lubricating fluid throughout the elastomer and in which crosslinking of the lubricating fluid to the elastomer components is minimized.

Lubricating fluid and elastomer can be physically blended by cutting, kneading or mixing with or without the application of heat. The blending step may be followed by a curing process as the lubricating fluid remains substantially free within the elastomer matrix.

Where the elastomer is thermoplastic, the blending step may include physically blending additional ingredients into the mixture, such as polypropylene, a binder, $BASO_4$, a filler, or polystyrene block compositions as long as biocompatibility of the lubricated elastomer is retained and the function of the elastomer as a multiply penetrable septa is not adversely affected. It is particularly important to ensure that the addition of the above identified elements do not result in a composition having a Shore A durometer hardness outside the 15 to 40 range. This is especially true with the addition of polypropylene that produces a stiffening effect upon the subject thermoplastic elastomer and reduces its elasticity. The blending step may be followed by applying heat in a typical range of 160 to 225 degrees centigrade to melt the mixture. A shearing pressure of at least 1500 p.s.i. may then be applied to the melted mixture to enhance dispersal of polysiloxane through the thermoplastic elastomer. The melting and pressure steps generally take place in an extruder which can also be used to mold the resulting composition into a desired shape and size. See, e.g. U.S. Pat. No. 4,578,413 to Sterling, incorporated above by reference in its entirety.

Internally lubricated elastomers of the present invention may also be made by a solvent infusion method in which an elastomer is contacted with a solvent solution in which a lubricating fluid is dissolved. The infused elastomer is removed from the solution and residual solvent is thereafter removed from the infused elastomer.

The solvent employed for infusion must solubilize a sufficient amount of the lubricating fluid to facilitate the infusion of the lubricating oil into the elastomer matrix. The solvent must be relatively inert to the elastomer material such that there is no unacceptable deterioration of the elastomer due to the solvent during the infusion step. The solvent should be volatile, such that it can be readily removed from the elastomer after the infusion step. It is believed that the solvent functions to expand the elastomer matrix and facilitates infusion of the lubricating fluid into that matrix.

During solvent infusion, the elastomer is contacted with the lubricating fluid solution for a sufficient time to allow the lubricating fluid to become substantially homogeneously dispersed throughout the elastomer at an initial level of from 0.5% to 50% by weight of the elastomer, but not to cause unacceptable deterioration of the elastomer material by the solvent. The speed of infusion of lubricating fluid into the elastomer depends on the type of elastomer, its composition and cure, the type and molecular weight of the lubricating fluid, the concentration of the lubricating fluid in the solvent, and the solvent chosen. The parameters of the method can be readily adjusted along with the contact time with the solution by one of ordinary skill in the art without undue experimentation using the guidance provided herein to achieve an initial desired lubricating fluid concentration in the elastomer. The maximum amount of a given lubricating fluid that can be infused into a given elastomer may be less than 50% by weight. In general, lower molecular weight lubricating fluids can be infused into an elastomer to a higher concentration than higher molecular weight lubricating oils. Thus a higher concentration of infused lubricating fluid can be obtained in a given elastomer, if desired, by employing a fluid having a lower molecular weight.

A variety of volatile organic solvents and particularly halogenated solvents can be used in the infusion method. Functional solvents include methylene chloride, ethanol and other low molecular weight alcohols, fluorocarbons, freons, and perchloroethylene. The solvent should not cause unacceptable deterioration of the elastomer over the time of exposure to the solvent solution. Methylene chloride is a preferred solvent for infusion of natural or synthetic rubbers with silicone oil.

Freshly washed or infused elastomer can be air-dried to remove solvent. To speed drying time, the infused elastomer can be dried at elevated temperature, or by application of a vacuum or both. Drying temperature should be controlled to avoid damage or degradation of the elastomer or the infused lubricating oil.

The solvent infusion method described herein results in an internally lubricated elastomer from which lower levels of undesirable organics are extractable into physiological fluids compared to untreated elastomer. It is believed that the solvent infusion treatment removes impurities from the elastomer which are dissolved in the solvent.

Contact with the solvent removes undesirable organics, such as residual curing or cross-linking agents, or accelerators, from the elastomer. Currently elastomers are most often cleaned of undesirable residues or impurities using water or aqueous surfactant solutions. These prior art methods effect only a surface cleaning of the elastomer, leaving behind undesirable organics which may later be extracted from the elastomer into physiological fluids.

The lubricating fluid is believed to be initially substantially uniformly dispersed in the elastomer employing the methods herein. After infusion or blending, the lubricating fluid may migrate within the elastomer, so that there is a gradient of distribution of fluid in the elastomer. It is known that silicone oils tend to migrate to the surface of the elastomer giving a somewhat enhanced concentration of silicone oil near the surface.

Internally lubricated elastomers of this invention and particularly those prepared by the solvent infusion method display significantly improved results in toxicity testing compared to analogous untreated elastomers. Silicone oil infused natural and synthetic rubbers display significantly improved results compared to analogous untreated rubbers in extraction tests.

Internally lubricated elastomers of this invention are useful in a number of medical and therapeutic applications as penetrable membranes or septa for infusion devices and like apparatus.

Solvent-cleaned and internally lubricated elastomers of this invention can be used to make septa for medical device applications. After treatment, elastomers can be cut or otherwise formed into a desired septum shape. Elastomers may also be formed into the desired shape prior to treatment; however, the increased volume of the elastomer resulting from lubricating fluid infusion must be taken into account. Typically, septa are circular disc elements about 0.3" to 0.4" thick. The thickness of a septum can be varied to adapt to the application and the properties of the elastomer.

Natural and synthetic rubbers and thermoplastic elastomers, having a Shore A durometer hardness in the range of 15 to 40 internally lubricated with silicone oil are good candidates for septum application. An exemplary application of an internally lubricated septum is as a septum in a fluid access site in a human infusion device.

FIG. 1 is a drawing of a fluid access site (20) for a human infusion system comprising the first preferred septum embodiment of this invention. The drawing shows the placement of the septum (1) in the body of the fluid access site. The access site has a housing (2) mounted on a base (3). The base optionally has slots (4) for receiving straps to allow the site to be strapped or attached to the patient or a support structure. The housing has two tubular arms (5) extending from a body (8) which form a passageway through the housing for flow of fluid through the access site. This passageway is the lumen of the site. The septum (1) provides a penetrable barrier between the external environment and the lumen. The arms (5) are provided with means for connecting to flexible medical tubing (6), for example luer connectors, by which the access site can be connected into a human infusion system such that fluid will pass from one tube through the lumen of the access site into the other tube.

The access site housing has two portions: a lower body portion (8) for receiving the septum and a cap portion (7) for holding the septum in sealing position. The cap portion has a circular aperture (11) in its top face. Once the cap portion is in position on the housing lower body, the aperture in the cap portion is completely covered by the septum. The circumference of the aperture in the cap is less than the circumference of the cap and the external face of the septum is exposed to the external environment while the internal face of the septum is in contact with the lumen. The septum forms the barrier between the lumen and the external environment. After the septum is inserted in the body portion, the cap portion is attached over the septum to the lower hollow cylindrical lower body portion. The cap portion can be snapped in place or can be attached to the lower body by an appropriate adhesive. The lower body portion (8) has a septum securing means, such as an indented lip, which contacts the perimeter of the internal face of the septum holding the septum in place against the aperture of the cap and forming a seal therewith. Once the cap portion is in place attached to the lower body portion, the fluid passageway through the body of the access site connecting to the two tubular arms (5) is formed and sealed from the external environment.

Figure 2:
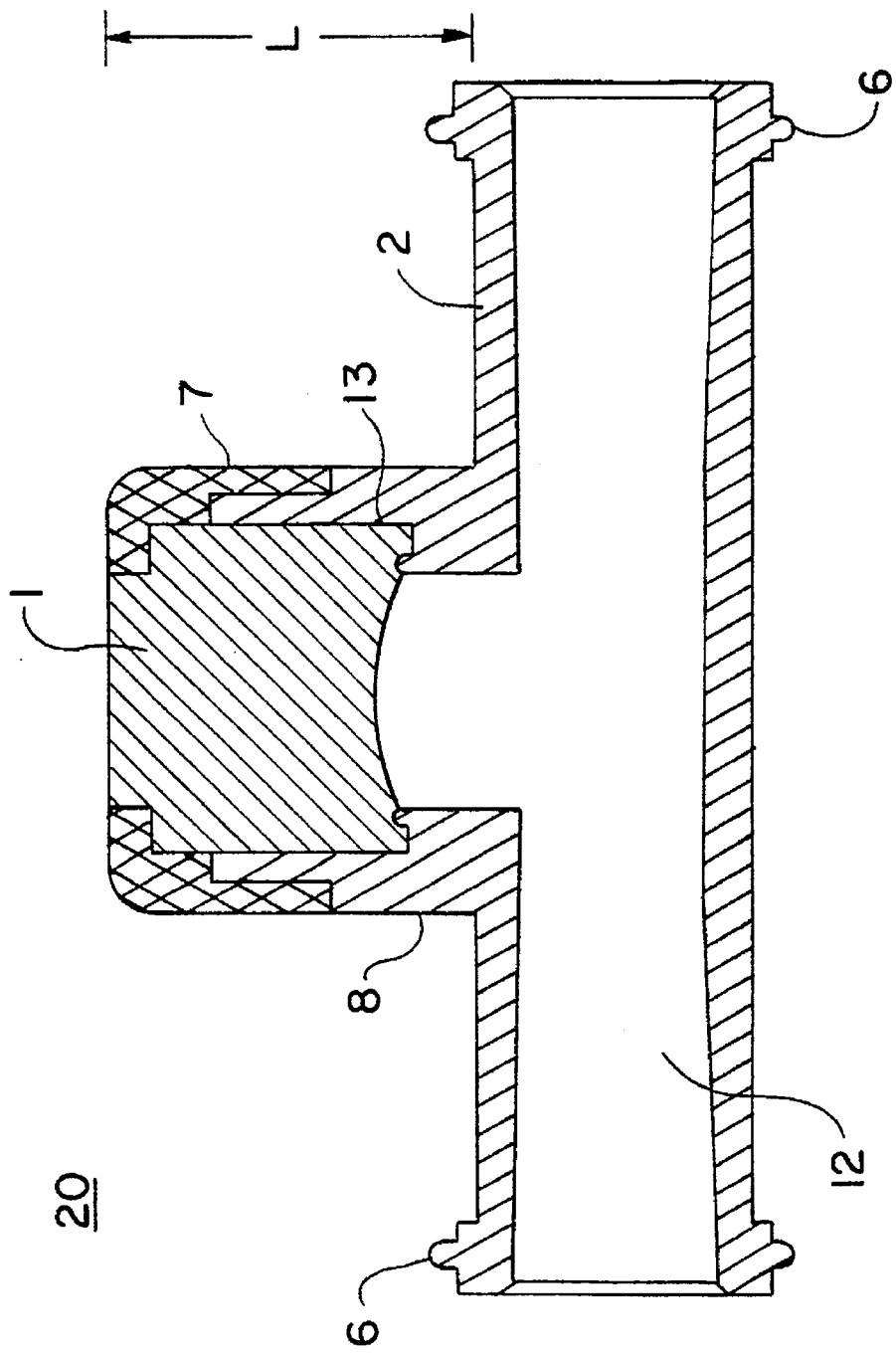
FIG. 2 is a schematic drawing of the cut-away view of the fluid access site of FIG. 1.

FIG. 2 is a cut-away view of the housing of the fluid access site of FIG. 1 showing the relative positions of the septum (1), cap (7) and body (8). The lower body has a lip (13) for holding the septum. When the cap is fixed in position over the body and septum, the septum is slightly compressed and forms a seal between the lumen (12) and the external environment. In operation, the lumen (12) is filled with fluid which can then be accessed by penetrating the septum with a syringe needle.

It has been discovered that the lifetimes of internally lubricated septa and non-lubricated septa are substantially dependent upon the depth of penetration of a syringe needle through the septum. In order to access fluid, the needle must penetrate through the septum but septum lifetime is substantially lengthened if the penetration depth of the needle is minimized. A uniform needle penetration depth was achieved by employing shielded needles, such as those of B-D Safety-Gard I.V. Hypodermic needles (Trademark, Becton-Dickensen). These hypodermic needles have a cylindrical plastic shield such that the needle is recessed within the shield when the needle is attached to a syringe. The shield has two opposing curved notches at the needle-end which fit against the tubular arms (5) of the fluid access site. The height of the housing above the tubular arm, L in FIG. 2, is chosen so that when the shielded syringe is positioned over the housing cap and the opposing curved notches of the shield engage the tubular arms of the housing, the syringe needle minimally penetrates the septum. The use of shielded needles in combination with the housing of FIG. 1 allows uniform minimal penetration of the septum and results in a substantially increased septum lifetime.

Piercing the septum with the needle of a syringe allows fluid to be withdrawn from or injected into the passageway in the access site and ultimately from the infusion system. If the infusion system is provided, as exemplified in infusion systems in U.S. Pat. Nos. 5,148,811, and 5,022,066, both of Messinger and 4,981,140 of Wyatt, which are herein incorporated by reference in their entirety, with a means for drawing a patient's blood into the infusion system and into the lumen of the access site, a blood sample can be taken through the septum in the access site. Similarly, medication, additional nutrients and other fluids can be introduced into the infusion system through the septum in the access site.

Figure 3:
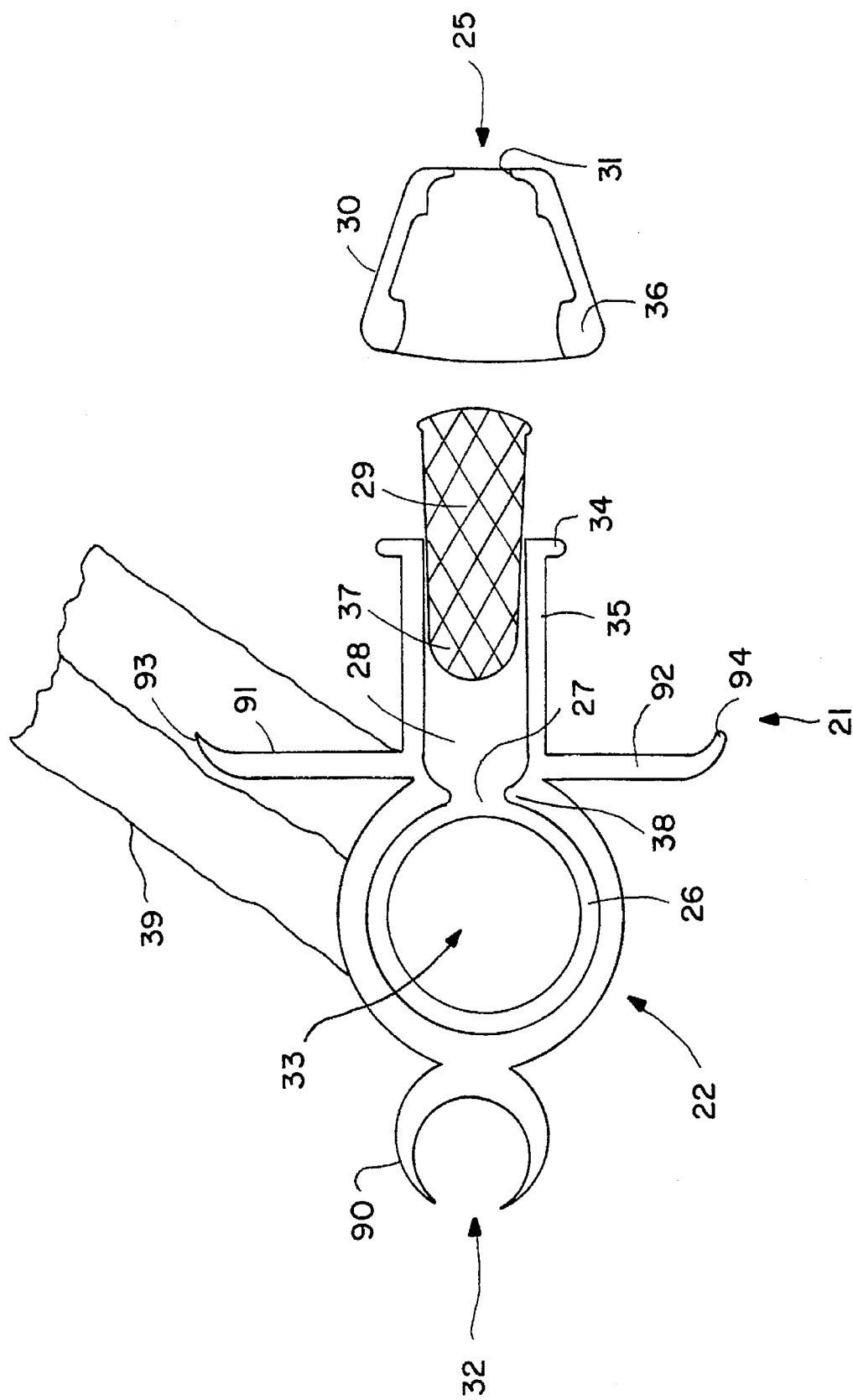
FIG. 3 is a cross sectional view of a second preferred embodiment of the present invention partially assembled.
Figure 5:
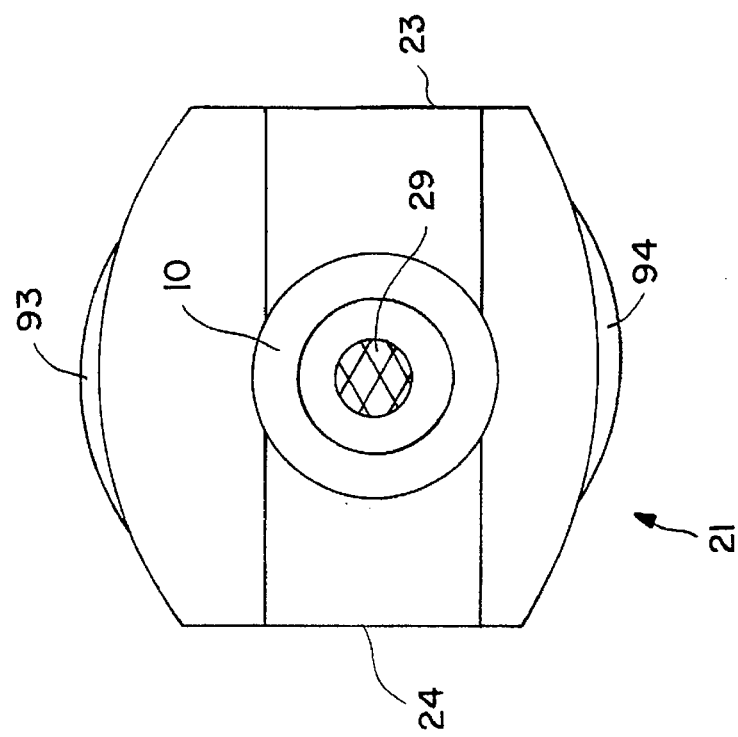
FIG. 5 is a plan view of the FIG. 3 preferred embodiment of the present invention.

Referring next to FIGS. 3 and 5, another embodiment of the present invention (21) provides a rigid housing (22) which connects to the tubing (39) of an extracorporeal tubing system thereby providing an access site (31) to the system. The tubing (39) may be secured in place by an adhesive, such as cyclohexanone, or by mechanical means, such as barbed fittings. Fluid can be added to, removed from or monitored in the system via this access site (31).

The housing (22) connects to the tubing system at the housing's first end (32) and provides access site (31) at its opposing end (25). In the preferred embodiment, the housing (22) is made of glycol modified polyester which is presently available through the manufacturer, Kodar. The housing (22), however, may also be constructed of other rigid materials.

Figure 8:
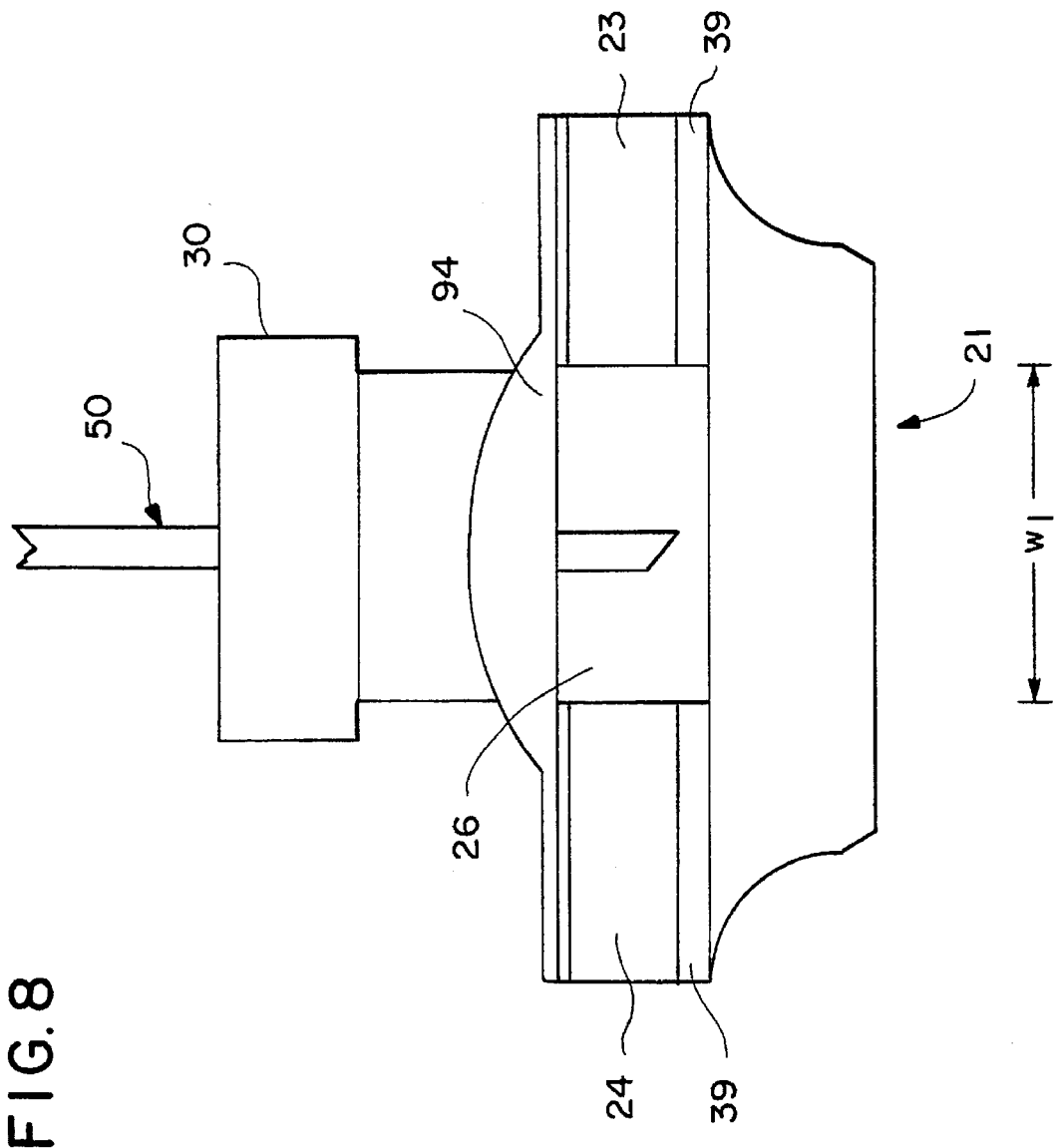
FIG. 8 is front view of the second embodiment of the present invention engaging a blunt needle.

The invention (21) is connected to the extracorporeal tubing system via two receiving portals (23, 24) best seen in FIG. 8. The first end (32) of the housing (22) forms a hollow cylindrical passage (33) having a longitudinal axis. A protruding annular stop (26) fixed in the center of the hollow cylindrical passage (33) separates the passage (33) into the two opposing portals (23, 24). The stop (26) comprises a width sufficient to accommodate a channel (27). Channel (27) is a hollow connecting passage as will be described further below.

Referring next to FIGS. 3, 5 and 8, each outer tube end (not shown) from the extracorporeal system enters a portal (23, 24) and abuts the protruding stop (26). The protruding annular stop (26) orients the two tube ends of tubing 39 into a facing orientation. The protruding annular stop (26) also separates the tube ends by the size of its width $W_1$. This separated, facing configuration allows the tube openings to communicate, thereby allowing the free flow of fluid between the tubes while leaving space for channel (27).

At its opposing end (25), the housing (22) provides a tubular cavity (28) surrounded by a cylindrical wall (35). The longitudinal axis of the tubular cavity (28) is oriented at a 90 degree angle to the longitudinal axis of the passage (33) formed on the housing's first end (32). The tubular cavity (28) is in fluid communication with the interior of the extracorporeal tubing system via the channel (27). The channel (27) is a hollow connecting passage bored through the stop (26). The channel (27) opens into a cavity (28) at one end and into the cylindrical passage (33) at its opposing end. The cavity (28) receives a elastomeric seal element (29) that acts as a barrier against contaminants.

The outer edge of the cylindrical wall (35) is encircled by an annular flange (34). A cap (30) fits tightly over the outer rim of the cylindrical wall (35) and cavity (28), thereby holding the plug (29) firmly in position. In the preferred embodiment, the cap (30) is constructed of polypropylene. The cap (30) can also be constructed of other rigid materials capable of maintaining compression of the seal element (29) through at least one sterilization procedure and normal use.

It is important that the cap (30) tightly maintain the seal element (29) under sufficient septum compression because without sufficient compression the septum does not reseal properly. Compression of the septum volume ranging from about 10% to about 25% has been found to be sufficient.

The cap (30) has a larger first diameter and tapers to a more narrow second diameter on its opposing end. The inner edge of the cap (30) located at the larger first diameter contains an annular lip (36). The larger first diameter slides over the annular flange (34) of the cylindrical wall (35). The annular lip (36) engages the corresponding annular flange (34) locking the cap (30) in place on the housing (22). At its more narrow second diameter, the cap (30) has an opening (31) for receiving a probe.

The elastomeric seal element (29) can be constructed of an internally lubricated thermoplastic elastomer. The thermoplastic elastomer is chosen to be easily penetrable while retaining sufficient flexibility, resealability, and tear strength to function adequately as a septum. Sufficient resealability is defined as the ability to prevent fluid from flowing through the septa (29) following at least six penetrations where each penetration occurs in substantially the same penetration site. Elastomers used for the present invention, should possess a hardness commensurate with a compression set appropriate for use in a penetrable septa that will be penetrated at least six times. A thermoplastic elastomer having a Shore A hardness ranging from 15 to 40, therefore, provides both ease of penetration and sufficient resealability for the useful life of the septum. Useful life is defined as the number of times a septa may be penetrated and still retain a satisfactory level of its desired characteristics such as low spallation and adequate resealability.

The septa embodiment of the present invention can be constructed of commercially available, injection moldable styrene-ethylene/butylene-styrene block copolymers, internally lubricated with polysiloxane, having Shore A durometer hardnesses ranging from 15 to 40. Polypropylene and mineral oil may also be added to the siloxane infused polymer composition as long as the resulting Shore A durometer hardness remains in the 15 to 40 range. The composition of this internally lubricated thermoplastic block copolymer is generally disclosed in U.S. Pat. Nos. 4,386,179 (1983), 4,481,323 (1984), 4,511,354 (1985), and 4,578,413 (1986) issued to Sterling, although compositions having Shore A hardness of 15 to 40 are not specifically discussed, the specifications of which incorporated by reference above. This internally lubricated thermoplastic block copolymer is available from Consolidated Polymer Technologies, Inc. Largo, Fla. under the name C-FLEX®. It is preferred that the C-FLEX® composition have a Shore A durometer hardness of 35. It is more preferred that the C-FLEX® composition have a Shore A durometer hardness of 18.

The seal element (29) can be easily and inexpensively formed by plastic injection molding. The seal element (29) is slightly tapered towards its first end (37), and must be substantially the size of the cavity (28) so that it forms a fluid tight seal with the cylindrical wall (35). The narrower first end (37) of seal element (29) is inserted into cavity (28) until it abuts the circular ledge (38).

The first end (32) of the housing (22) also comprises a cylindrical clip (90) for anchoring the assembled housing (2), and tubing (39) into position on cylindrical members (not shown) such as additional tubing or support posts (not shown). The housing (22) also comprises two protruding arms (91, 92) that extend outward from the housing (22) at substantially the housing junction of the cavity (28) and the cylindrical passage (33). The protruding arms (91, 92) comprise finger flanges (93, 94) at their distal edges. The finger flanges (93, 94) function to protect a user's fingers from injury or puncture if the probe should slip or accidentally disengage from the septum (29).

Figure 4:
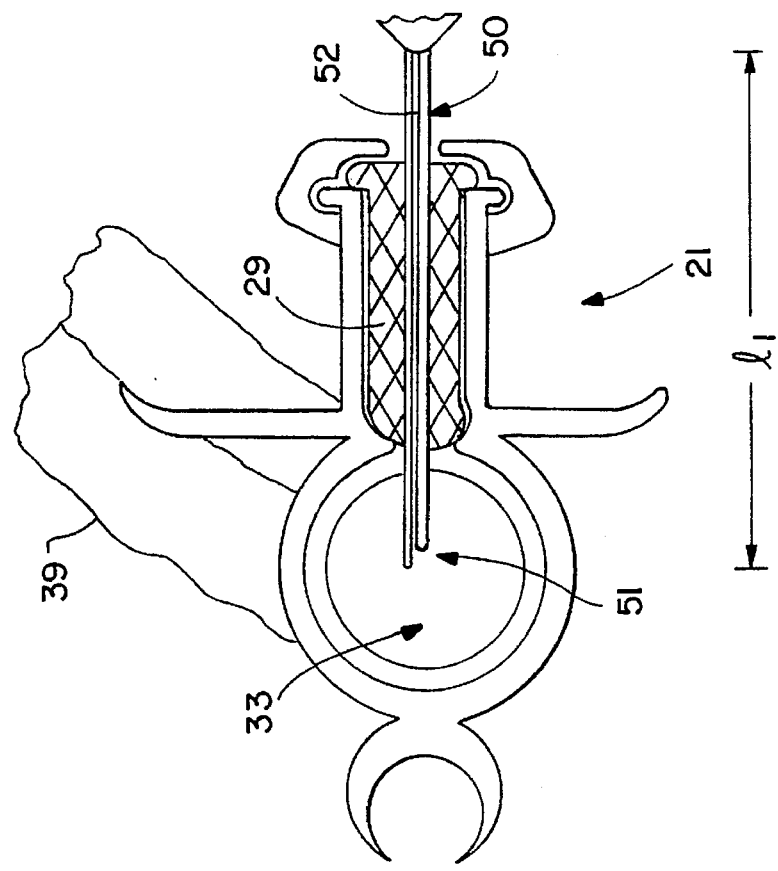
FIG. 4 is a cross sectional view of the second preferred embodiment of the present invention fully assembled and engaging a blunt needle.

Referring next to FIG. 4, a side sectional view of the fully assembled invention engaging a blunt probe 50 is shown. The probe (50) is an elongated, cylindrical, implement with an interior passage (52) extending throughout its entire length. The tip (51) of the blunt probe (50) is bevelled at a 45 degree angle and then tumbled to remove any sharp edges as shown in FIG. 7. The tip (51) of the probe is substantially blunt such that the tip (51) won't penetrate skin unless a pressure greater than that used to penetrate the probe through the septa is exerted on the probe (50). The probe (50) can be constructed of metal, such as steel. A 20 gauge needle or smaller may be used with the present invention.

The probe (50) begins entry into the tubular cavity (28) via the cap opening (31). Pressure is then applied to the probe (50) forcing it to penetrate through the entire length of the seal element (29). The probe (50) is then extended through channel (27) and into the interior of the extracorporeal tubing system; thus, fluid can be added to, removed from or monitored within in the extracorporeal system. A shielded needle is not required with this embodiment because the length $l_1$ of the blunt needle (50) is limited to prevent the blunt needle (50) from penetrating the seal element (29) farther than necessary. The blunt needle may comprise a length $l_1$ of about 0.5 inches.

Referring next to FIG. 6 a side plan view of the fully assembled present invention engaging a sharp probe (70) is shown. The probe (70) is once again an elongated, cylindrical implement with an interior passage (72) extending throughout its length. The tip (71) of the probe is sharp as is common with conventional hypodermic needles. The probe (70) is constructed of metal, such as steel. The probe (70) can be a standard syringe needle comprising a gauge 20 or smaller. The probe (70) is forced through the seal element (29) and used as described for the blunt probe of FIG. 4. The penetration of the sharp probe 70 through the seal element (29) is limited by the wall 73 of the passage 33.

It has been visually observed that a sharp or blunt probe, having a gauge of 20 or smaller, does not core or gall the C-FLEX® septum (29), having a Shore A durometer hardness of about 15 to 40, in a FIG. 3 access site, until the probe has penetrated the septa (29) more than ten times at the same insertion site.

The access site of FIGS. 1 and 3 are only two examples of the possible uses of the septa of this invention. In general the septa of this invention can be employed in any medical or therapeutic device application requiring a penetrable seal and particularly in applications for disposable devices or apparatus in which the penetrable seal need not be in extended contact, not over about 72 hours, with tissue or body fluids.

EXAMPLES

Example 1: Infusion of Isoprene Rubber with Silicone Oil

Polyisoprene rubber septa (about 85 g, Product No. 100-35, Gardena Rubber Co., Gardena, Calif.) were placed in about 750 ml of a shaken 10% (V/V) solution of silicone oil in methylene chloride. Silicone oil solutions that are discolored, cloudy or contain black debris particles are unacceptable for use and should be discarded. Septa were soaked for at least 1 hour, but not more than 24 hours. The soaking time is limited in order to avoid deterioration of the septum material by the solvent. After soaking, the septa were removed from the solvent solution. Methylene chloride was then removed from the septa. The septa were either dried at room temperature for at least 24 h. or dried for about 24 h. on trays in an oven at about 60° C. Dependent on the molecular weight of the silicone oil used, from about 0.5% to about 15% by weight of silicone oil could be infused into polyisoprene septa using this solvent infusion method.

Example 2: Septum Leakage and Other Comparison Tests

Test fluid access sites containing test septa are constructed and subjected to one sterilization cycle. The test sites are then connected with tubing into a single hydraulic circuit. The tubing and injection site passageways are filled with a saline solution, bubbles are removed from the system, and the fluid system is pressurized to 100–550 mm Hg to check for leaks. Any leaking sites are replaced or adjusted. Durability of septa is tested by repeated punctures of each septum with a syringe and needle. A new needle is employed for each septum puncture. The time between consecutive punctures of a septum is at least 30 m. Shielded hypodermic needles (B-D Safety-Gard I.V. [Trademark] Becton-Dickensen Co.) are employed so that the needle penetrates through the septum to the same extent on every puncture. After each puncture, the septum is observed for leaks and other indicia of deterioration. In addition, after each puncture the needle is examined for obstruction of flow which indicates coring of the septum. Observation of a leak is scored as a septum failure. In addition, if obstruction of a needle is observed on two consecutive punctures of the same septum, that septum fails. After the desired number of punctures have been performed, the access sites can be disassembled and the internal face of the septum can be examined for excessive cracking, splitting or any other failure.

Synthetic polyisoprene rubber septa infused with a methylene chloride solution of silicone oil (50 cs) as described in Example 1, on average, will show significantly better performance in this durability test than analogous untreated polyisoprene rubber septa. Natural rubber septa infused with a methylene chloride solution of silicone oil (50 cs) as described in Example 1, on average, will show significantly better performance in this durability test than analogous untreated natural rubber septa.

Natural rubber and synthetic polyisoprene rubber septa infused with silicone oil as described in Example 1 display significantly lower levels of physiological fluid-extractable materials than analogous untreated rubber septa. Silicone-infused rubber septa of this invention display significantly improved properties compared to untreated rubber when subjected to a variety of toxicology tests.

Example 3: Additional Elastomeric Septa Leakage Tests

Fluid access sites containing C-FLEX® test septa, having a Shore A durometer hardness of 35, and a polypropylene cap, are constructed and subjected to two sterilization cycles. The fluid access sites are then placed in an environmental chamber and cycled through four 4 hour thermal cycles of 60 degrees centigrade and 95% humidity to minus 20 degrees centigrade and 50% humidity over a period of 32 hours. Exposing the access sites to thermal cycling forces any stress relaxation which may occur in the septum material over time. The test sites are then connected with tubing into a single hydraulic circuit.

The tubing and injection sites are pressurized to about 750 millimeters of mercury ("mmHg") and submerged in a water bath to check for resulting positive pressure leaks. A positive pressure leak is detected when a continuous stream of bubbles or a growing bubble is observed when the access site is submerged. Observation of a leak is scored as a septum failure. Three hundred and sixty access sites were tested. No failures were observed.

The access sites are dried off and filled with a glycerol/water solution that is at 37 degrees centigrade under +400 mmHg of pressure. Durability of septa is tested by repeated punctures of each septum with a 20 gauge sharp needle (manufactured by either Becton-Dickensen Co. or Terumo) using a puncturing jig. A new needle is employed for each septum puncture. The needle is removed and the septum wiped. The access site is observed for leaks for 5 seconds. A leak is detected where a continuing flow of fluid from the septum is observed during a five second period after the needle has been removed and the septum has been wiped dry. This procedure is repeated five more times, inserting the needle into the same puncture position each time. Observation of a leak is scored as a septum failure. Three hundred and sixty access sites were tested. No septum failures were observed.

Results of the foregoing procedures revealed that fluid access sites containing C-FLEX® test septa, having a Shore A durometer hardness of 35 did not stress relax under thermal cycling, leak under positive pressure and comprise a durability to withstand at least 6 penetrations at the same insertion point without leaking.

Example 4: Simulated Dialysis Leak Test

The fluid access sites previously tested for leakage as described above in Example 3 are filled with a glycerol/water solution that is at 37 degrees centigrade under about +400 mm Hg of pressure. A 20 gauge sharp unshielded needle, occluded by a male luer cap, is inserted into each septum of each access site. The glycerol/water solution is circulated through the hydraulic circuit for 7 hours at 37 degrees centigrade under about 400 mmHg of pressure. The access sites are observed for leaks immediately after the 7 hour test. A leak is detected when a growing droplet or continuous stream of liquid flowing out of the needle insertion point is observed, over a five second period, while the needle remains inserted in the septum. Observation of a leak is scored as a septum failure. Three hundred and sixty access sites were tested. No failures were observed.

The access sites are next filled with a degassed glycerol/water solution at 37 degrees centigrade. The glycerol solution is circulated through the access sites at the subatmospheric pressure of about −600 mmHg for 10 to 12 minutes. The access sites are observed for leaks over a period of five seconds. A leak is detected when a stream of air bubbles is observed entering the tubing set at the point of needle insertion. Observation of a leak is scored as a septum failure. Three hundred and sixty access sites were tested. No failures were observed.

The access sites and tubing are drained of fluid and pressurized with air to about +600 mmHg. The access sites, having the imbedded needles, and tubing are submerged in a water bath and observed for a period of five seconds for leaks. A leak is detected where a continuous stream of bubbles or a growing bubble is observed. Observation of a leak is scored as a septum failure. Three hundred and sixty access sites were tested. No failures were observed.

Fluid access sites containing C-FLEX® test septa, having a Shore A durometer hardness of 35 did not leak after a seven hour simulated dialysis procedure. The fluid access sites did not leak when subjected to subatmospheric pressure of approximately −600 mmHg following thermal cycling, leak testing as described in Example 3, and a seven hour simulated dialysis run. The fluid access sites also did not leak when subjected to a positive pressure of approximately +600 mmHg following thermal cycling, leak testing as described in Example 3, a seven hour simulated dialysis run, and subatmospheric pressure leak testing.

While the invention has been shown and described with respect to a specific embodiment thereof, this is intended for illustration rather than limitation, and other variations and modifications of the specific device shown will be apparent to those skilled in the art all within the intended spirit and scope of the invention. Accordingly, the patent is not to be limited in scope and effect to the specific embodiments shown and described herein, nor in any other way that is inconsistent with the extent to which the progress in the art has been advanced by the invention.

We claim:

1. An internally lubricated septum comprising an elastomeric composition having a lubricating fluid dispersed there through, and a predetermined hardness wherein said predetermined hardness renders said elastomeric composition capable of use as a penetrable seal for a plurality of penetrations.

2. The internally lubricated septum of claim 1, wherein said elastomer is a polyurethane, a polyolefin or a thermoplastic elastomer.

3. The internally lubricated septum of claim 1, wherein said elastomer is silicone elastomer.

4. The internally lubricated septum of claim 1, wherein said elastomer is a natural or synthetic rubber.

5. The internally lubricated septum of claim 4, wherein said lubricating fluid is a silicone oil.

6. The internally lubricated septum of claim 5, wherein said silicone oil is present in said rubber at a level of about 0.5% to about 50% by weight.

7. The internally lubricated septum of claim 5, wherein said silicone oil is present in said rubber at a level of about 1% to about 15% by weight.

8. The internally lubricated septum of claim 5, wherein said silicone oil is a silicone oil having an average molecular weight of from about 1200 to about 62,000.

9. The internally lubricated septum of claim 5, wherein said silicone oil has a viscosity of about 20 to 100 cs.

10. The internally lubricated septum of claim 9, wherein said silicone oil has a viscosity of about 50 cs.

11. The internally lubricated septum of claim 5, wherein said silicone oil is a polydiphenylsiloxane.

12. The internally lubricated septum of claim 5, wherein said silicone oil is a polydimethylsiloxane.

13. The internally lubricated septum of claim 12, wherein said silicone oil is present in said rubber at a level of about 1% to 15% by weight.

14. The internally lubricated septum of claim 1, wherein said lubricating fluid has a viscosity of about 20 to 100 cs.

15. The internally lubricated septum of claim 1, wherein said lubricating fluid is a mineral oil.

16. The internally lubricated septum of claim 1, wherein said lubricating fluid is a fluorocarbon oil.

17. The internally lubricated septum of claim 5, wherein said elastomer is a peroxide-cured polyisoprene synthetic rubber.

18. The internally lubricated septum of claim 5, wherein said elastomer is a sulfur-cured polyisoprene synthetic rubber.

19. The internally lubricated septum of claim 1, wherein said predetermined hardness comprises a Shore A durometer hardness ranging from about 15 to about 40.

20. The internally lubricated septum of claim 2, wherein said predetermined hardness comprises a Shore A durometer hardness ranging from about 15 to about 40.

21. The internally lubricated septum of claim 20, wherein said thermoplastic elastomer is a styrene-ethylene/butylene-styrene block copolymer.

22. The internally lubricated septum of claim 21, wherein said lubricating fluid is a silicone oil.

23. The internally lubricated septum of claim 22, further comprising mineral oil.

24. The internally lubricated septum of claim 3, wherein said predetermined hardness comprises a Shore A durometer hardness ranging from about 15 to about 40.

25. The internally lubricated septum of claim 7, wherein said predetermined hardness comprises a Shore A durometer hardness ranging from about 15 to about 40.

26. A human infusion apparatus having a fluid access site comprising the septum of claim 1.

27. A human infusion apparatus having an fluid access site comprising the septum of claim 5.

28. A human infusion apparatus having a fluid access site comprising an internally lubricated septum of claim 5, further comprising a synthetic isoprene rubber having silicone oil dispersed there through wherein said silicone oil has a viscosity of about 50 cs and said silicone oil is present in said rubber at a concentration from about 1% to 15% by weight.

29. An elastomer suitable for use in contact with human tissue or body fluids having a silicone oil dispersal there through wherein said silicone oil is present in said elastomer at a level of about 1% to 15% by weight and wherein said silicone oil is dispersed in said elastomer by contacting said elastomer with a solution of said silicone oil in a volatile organic solvent followed by removal of said solvent from the elastomer.

30. An elastomer suitable for use in contact with human tissue or body fluids having a silicone oil dispersed there through wherein said silicone oil is dispersed in said elastomer by contacting said elastomer with a solution of said silicone oil in a volatile organic solvent wherein said solvent is methylene chloride or perchloroethylene.

31. A method for cleaning an elastomer comprising the steps of contacting an elastomer with an organic solvent for a sufficiently long time to remove undesirable organics followed by removing residual organic solvent from said elastomer.

32. The method of claim 31, in which the solvent is methylene chloride.

33. The method of claim 31, wherein the elastomer is a peroxide-cured polyisoprene.

34. A method for preparing an improved elastomer for medical and therapeutic devices comprising the steps of contacting an elastomeric material with a solution of lubricating fluid in methylene chloride followed by removing residual methylene chloride from said material.

35. The method of claim 34, wherein said elastomeric material is a natural or synthetic rubber.

36. The method of claim 34, wherein said lubricating fluid is a silicone oil.

37. The method of claim 34, wherein said elastomeric material is contacted with said solution for about 4 to 8 hours.

38. The method of claim 34, wherein said residual solvent is removed from said elastomer by application of a vacuum.

39. A method for preparing an improved septum for application to medical or therapeutic devices comprising the steps of contacting a penetrable elastomeric material with a solution of a lubricating fluid in a volatile organic solvent followed by removing residual solvent from said material.

40. The method of claim 39, wherein said elastomeric material is a natural or synthetic rubber.

41. The method of claim 39, wherein said lubricating fluid is a silicone oil.

42. The method of claim 39, wherein said solvent is methylene chloride.

43. The method of claim 39, wherein said elastomeric material is contacted with said solution for about 4 to 8 hours.

44. The method of claim 39, wherein said residual solvent is removed from said elastomer by application of a vacuum.

45. An access device for an extracorporeal tubing system, said extracorporeal tubing system having an interior, comprising:

means for accessing said extracorporeal tubing system;

means, disposed inside said accessing means having a continuous un-pierced surface, for protecting said interior of said extracorporeal tubing system from a plurality of contaminants, said protecting means comprising a thermoplastic elastomeric material having a lubricating fluid dispersed there through; and means, having a substantially blunt end, for penetrating said continuous un-pierced surface of said protecting means, functioning to create a transient, self-sealing opening in said protecting means to allow monitoring, injection and removal of a fluid contained in said extracorporeal tubing system.

46. The access device of claim 45, wherein said protecting means further comprises a Shore A durometer hardness in a range of about 15 to about 40.

47. The access device of claim 46, wherein said thermoplastic elastomer comprises a styrene-ethylene/butylene-styrene block copolymer.

48. The access device of claim 46, wherein said lubricating fluid comprises a silicone oil.

49. The access device of claim 48, wherein said lubricating fluid further comprises a mineral oil.

50. The access device of claim 49, wherein said thermoplastic elastomer further comprises polypropylene.

51. The access device of claim 46, wherein said penetrating means further comprises a hollow cylindrical probe having a tip, said tip having edges cut at a 45 degree angle and said edges are bevelled.

52. A process for accessing an interior of an extracorporeal tubing system, comprising the steps of:

internally lubricating a thermoplastic elastomer with a lubricant thereby creating a thermoplastic composition, said thermoplastic composition having a predetermined hardness for use as a penetrable seal for multiple penetrations; and molding said thermoplastic composition into said penetrable seal for receiving a substantially blunt or sharp probe.

53. The process of claim 52, further comprising the step of compressing said penetrable seal in a cavity of a housing of an access site for an extracorporeal tubing system.

54. The process of claim 53, wherein said predetermined hardness comprises a Shore A durometer hardness ranging from about 15 to about 40.

55. The process of claim 54, wherein said thermoplastic elastomer comprises a styrene-ethylene/butylene-styrene block copolymer.

56. The process of claim 54, wherein said thermoplastic composition further comprises polypropylene.

57. The process of claim 56, wherein said lubricant further comprises a silicone oil.

58. The process of claim 57, wherein said lubricant further comprises a mineral oil.

59. The process of claim 58, wherein said molding step further comprises:

heating said thermoplastic composition; and extruding under pressure said thermoplastic composition into septa having a predetermined shape and size.

60. The process of claim 59, wherein said silicone oil further comprises polysiloxane.

61. A method for accessing an extracorporeal tubing system comprising the steps of penetrating a probe through a penetrable septum, said septum having a Shore A durometer hardness ranging from about 15 to 40 and comprising an internally lubricated thermoplastic elastomer.

62. The method of claim 61, wherein said internally lubricated thermoplastic elastomer comprises a styrene-ethylene/butylene-styrene block copolymer.

63. The method of claim 62, wherein said internally lubricated thermoplastic elastomer further comprises polypropylene.

64. The method of claim 63, wherein said internally lubricated thermoplastic elastomer further comprises mineral oil.

65. The method of claim 64, wherein said internally lubricated thermoplastic elastomer further comprises a silicone oil lubricant.

66. The method of claim 65, wherein said silicone oil lubricant further comprises polysiloxane.

67. The method of claim 66, wherein said penetrating step further comprises selecting said probe to have a substantially blunt tip.

68. An access device for an extracorporeal tubing system, said extracorporeal tubing system having an interior, comprising:

means for accessing said extracorporeal tubing system; and means, disposed inside said accessing means having a continuous un-pierced surface, for protecting said interior of said extracorporeal tubing system from a plurality of contaminants, said protecting means comprising a thermoplastic elastomeric material having a lubricating fluid dispersed there through.

69. A human infusion apparatus comprising an access site; said access site having a septum wherein said septum is composed of a thermoplastic elastomeric material having a lubricating fluid dispersed there through.

70. A septum comprising an elastomeric composition having a lubricating fluid dispersed there through, said septum having an increased useful lifetime as a result of the use of the internally lubricated elastomeric composition.

* * * * *